United States Patent [19]

Fein et al.

[11] 4,058,462
[45] * Nov. 15, 1977

[54] SYSTEM FOR SUSTAINED RELEASE OF PHENOLIC MATERIAL FROM POROUS GRANULES OF INSOLUBLE POLYMERIC PHENOLIC COMPLEXES

[75] Inventors: Marvin M. Fein, Westfield, N.J.; Earl P. Williams, Pen Argyl, Pa.; Nathan D. Field, Wyckoff, N.J.

[73] Assignee: GAF Corporation, New York, N.Y.

[*] Notice: The portion of the term of this patent subsequent to Oct. 21, 1992, has been disclaimed.

[21] Appl. No.: 623,382

[22] Filed: Oct. 17, 1975

Related U.S. Application Data

[63] Continuation-in-part of Ser. No. 25,249, April 2, 1970, abandoned, which is a continuation-in-part of Ser. No. 436,609, Jan. 25, 1974, Pat. No. 3,914,187.

[51] Int. Cl.$^2$ .............................................. B01D 25/06
[52] U.S. Cl. .................................................. 210/289
[58] Field of Search ................ 137/268; 210/266, 282, 210/283, 446, 287, 289; 260/2.5 B

[56] References Cited

U.S. PATENT DOCUMENTS

| | | | |
|---|---|---|---|
| 2,341,429 | 2/1944 | Elsey | 210/446 |
| 2,773,601 | 12/1956 | Keller et al. | 210/266 |
| 3,914,187 | 10/1975 | Fein et al. | 260/2.5 B |

Primary Examiner—Wilbur L. Bascomb, Jr.
Assistant Examiner—Ivars Cintins
Attorney, Agent, or Firm—Walter C. Kehm; Marilyn J. Maue

[57] ABSTRACT

A system for sustained release of phenolic material into a fluid from phenolic complexes of water-insoluble, but water-swellable crosslinked N-vinyllactam or N-alkyl-N-vinylamide polymers in the form of porous beads or granules. The complexes, which are particularly suited for use in situations wherein fluids containing phenolic materials in limited quantities are desired, and are provided by leaching a limited amount of phenolic material from the complex by contacting the porous granules in a container, such as in a canister or column which is used to treat liquids or water.

10 Claims, 5 Drawing Figures

SYSTEM FOR SUSTAINED RELEASE OF PHENOLIC MATERIAL FROM POROUS GRANULES OF INSOLUBLE POLYMERIC PHENOLIC COMPLEXES

This application is a continuation-in-part of application Ser. No. 25,249 filed Apr. 2, 1970, now abandoned and copending application Ser. No. 436,609 filed Jan. 25, 1974, now U.S. Pat. No. 3,914,187.

The instant invention is directed to a system of utilizing novel phenolic-polymeric complexes. In particular, the instant invention is directed to gradual and sustained release of phenolic material into a fluid from novel phenolic-crosslinked N-vinyllactam or N-alkyl-N-vinylamide polymers in the form of porous beads or porous granules which are contained in a container into which the fluid is passed for contact with said granules.

For many years water insoluble powders of polyvinyl pyrrolidone, similar lactams, and similar vinylamides were utilized for a variety of purposes including among others as filtering media in packed column and similar filtration purification systems. The powdered materials, however, are unsatisfactory in most instances because of the extremely long drainage time of liquid through the powder. Accordingly, it has long been the desire to provide an improved product which will eliminate such deficiency.

In copending application Ser. No. 436,608 it has been found that the new products may be prepared through the preparation of phenolic complexes of water-insoluble but water-swellable cross-linked N-vinyllactam or N-alkyl-N-vinylamide polymers in the form of porous beads or porous granules.

In this connection, it has been found in accordance with the instant invention that a sustained system for the release of phenolic material from such porous bead-like phenolic complexes are of particular use in a wide range of applications and, in particular, in those applications wherein a phenolic material is desired, but in limited quantity over an extended period of time. That is to say, that the porous polymeric granules of the instant invention as a result of the complexing with phenolic materials establish an equilibrium characteristic which beneficially releases said phenolic material in limited quantities. Therefore, said materials are ideally suited for use in canisters and/or columns where they may be used either to treat liquids such as beverages and/or water or in processes wherein liquids are treated by diffusion through the bead bed. In such processes, release of the phenolic material of the complex may be regulated through control of the equilibrium relationship and the flow rate of the liquid through the container.

Therefore, it is an object of the instant invention to provide a novel and sustained system for the release of phenolic material from said complex which is particularly suited for use in applications wherein controlled quantities of phenolic material are necessary over an extended period of time.

A still further object of the instant invention is to provide a system for releasing phenolic material in controlled amount into water or beverages.

These and other objects of the instant invention will be more evident from the following more detailed description thereof.

The phenolic complex of a water-insoluble, but water-swellable crosslinked N-vinyllactam or N-alkyl-N-vinylamide which polymeric material, in the form of either porous beads or porous granules is prepared as follows.

The N-vinyllactams employed in the preparation of the crosslinked polymers of the phenolic complexes of the present invention are lactams corresponding to the general formula:

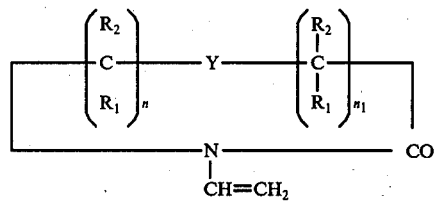

where $R_1$ and $R_2$ = hydrogen, alkyl and aryl

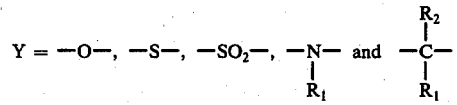

$n$ and $n_1$ range from 0 to 5, but where only one of the $n$ or $n_1$ values may be zero.

Such N-vinyllactams are those which can be prepared, for example, by the vinylation of lactams such as disclosed in U.S. Pat. Nos. 2,891,058; 2,265,450; 2,334,454 and 3,097,087. Similarly, the N-vinyl lactams may be prepared in a known manner by N-vinylation of the corresponding lactams at elevated temperatures in a manner such as disclosed in U.S. Pat. No. 2,317,084. Accordingly, representative N-vinyl lactams operable in accordance with the present invention include such as: N-vinyl-2-pyrrolidone and N-vinyl-substituted derivatives of the following lactams: 3,3-dimethyl-2-pyrrolidone, 4,4-dimethyl-2-pyrrolidone, 3,4-dimethyl-2-pyrrolidone, 3-ethyl-2-pyrrolidone, 3,5-dimethyl-2-pyrrolidone, 3-phenyl-2-pyrrolidone, 4-acryl-2-pyrrolidone, 5-ethyl-2-pyrrolidone, 3-methyl-2-pyrrolidone, 4-methyl-2-pyrrolidone, 5-methyl-2-pyrrolidone, 3,3,5-trimethyl-2-pyrrolidone; 2-piperidone, 5,5-diethyl-2-piperidone, 5,6-dimethyl-2-piperidone, 4-ethyl-2-piperidone, 6-ethyl-2-piperidone, 6-ethyl-3-methyl-2-piperidone, 3-methyl-2-piperidone, 4-methyl-2-piperidone, 5-methyl-2-piperidone, 6-methyl-2-piperidone; 2-caprolactam, 3,6-dimethyl-2-caprolactam, 4,6-dimethyl-2-caprolactam, 4,7-dimethyl-2-caprolactam, 7,7-diethyl-2-caprolactam, 3-ethyl-2-caprolactam, 5-ethyl-2-caprolactam, 6-ethyl-2-caprolactam, 7-ethyl-2-caprolactam, 4-ethyl-6-methyl-2-caprolactam, 6-ethyl-4-methyl-2-caprolactam, 3-methyl-2-caprolactam, 4-methyl-2-caprolactam, 5-methyl-2-caprolactam, 6-methyl-2-caprolactam; 2-oxazinidinone (e.g. U.S. Pat. Nos. 2,905,669 and 3,097,087), 5-ethyl-2-oxazinidinone, 5-phenyl-2-oxazinidinone, 4,5-dimethyl-2-oxazinidinone, 5,5-dimethyl-2-oxazinidinone, 2,5-diphenyl-2-oxazinidinone, 2-phenyl-4-oxothiazolidone, 2,2'-diphenyl-4-oxothiazolidone, 2,2'-dimethyl-4-oxothiazolidone; 2-oxazolidinone (deriv. in U.S. Pat. No. 2,905,690 and 2,891,058), 5-methyl-2-oxazolidinone, 4-methyl-2-oxazolidinone, 5-ethyl-2-oxazolidinone, 4,5-dimethyl-2-oxazolidinone, 2-phenyl-2-oxazolidinone, 5-butyl-2-oxazolidinone, 5-propyl-2-oxazolidinone, 4,5-diethyl-2-oxazolidinone; 3-morpholinone disclosed in U.S. Pat. No. 2,987,509, e.g., 5-methyl-3-morpholinone, 5-ethyl-3-morpholinone; 3,5-dimethyl-3-morpholinone; 2- piperazinone (e.g. JACS 62, 1202 (1940)), the 3,3-dimethyl-2-ketopiperazine, 3-methyl-2-ketopiperazine; 4-thiazolidone (e.g. JACS 76, 578 (1954)), 2-methyl-4-thiazolidinone; 2-phenyl-4-thiazolidinone; 2-phenyl-4-thiazolidinone dioxide; 2-thiazolidone (J. Chem. Soc. 1949, 2367); 3-thiamorpholinone; 2-pyrimidone (e.g., J. Chem. Soc. 1959, 525); 2-imidazolidones (e.g. Ann. 232, 1222 (1885)); N,N-ethylene-thioureas (e.g. J. Biol. Chem. 163, 761 (1946); tetrahydro-(2H, 1,3)-oxazin-3-ones (e.g., U.S. Pat. No. 2,940,971), and the like.

Similarly, suitable N-alkyl-N-vinylamides useful in accordance with the present invention are those which correspond to the formula:

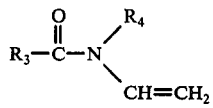

wherein R₃ and R₄ are independently selected from the class of hydrocarbon radicals of 1 to 4 carbon atoms preferably 1 to 2 carbon atoms.

Such N-alkyl-N-vinylamides are illustrated in U.S. Pat. No. 3,214,370, exemplary amides being: N-methyl-N-vinyl-acetamide, N-ethyl-N-vinylacetamide, N-butyl-N-vinylacetamide, N-methyl-N-vinylpropionamide, N-methyl-N-vinylpentanoic acid amide, N-methyl-N-vinylformamide and the like.

In preparing the porous granular or porous bead form of polymer in accordance with the present invention, the N-vinyllactam or N-alkyl-N-vinylamide, with or without a further copolymerizable monomer and with a crosslinking agent as to be hereinafter defined, is polymerized in a manner described in co-pending applications Ser. No. 736,302 filed June 12, 1968 and Ser. No. 875,516 filed Nov. 10, 1969. In this connection, as defined in such co-pending applications the porous granular or bead form of the polymer is produced from a suspension polymerization system wherein the lactam or amide monomer with optional copolymerizable monomer and crosslinking agent is polymerized in an aqueous solution of an electrolyte, the suspension being maintained during polymerization by mechanical means. In such polymerization process a free radical polymerization source is utilized.

In this regard, the preparation of the porous bead or porous granular form of polymer involved the polymerization of the N-vinyl lactam or N-alkyl-N-vinylamide with an amount of crosslinking agent, i.e., divinyl monomer within the range of about 0.1% to about 20% by weight based on the weight of the N-vinyl lactam or N-alkyl-N-vinylamide. Such polymerization is carried out in an aqueous solution of an electrolyte, the concentration of electrolyte being high enough to produce phase separation before or during polymerization. In this regard, a preferred electrolyte solution contains from about 10% to about 20% sodium sulfate. Since the monomers polymerized in accordance with this procedure are not very soluble in such electrolyte solutions, by using more than enough monomers to saturate the solution of electrolyte a suspension of the excess monomers can be made through mechanical agitation. In this connection, the use of excess undissolved salt is often beneficial since the solid becomes enmeshed in the bead or granule and upon dissolution increases the surface area of the porous product.

In the polymerization process, the relative proportion of total monomer to water is determined at the upper limit by the ability of heat removal and the danger of particle agglomeration, this upper limit being as high as about 80% monomer, preferably about 50% monomer based upon the weight of the water. The lower limit is inter alia based on convenience of operating without undue bulk, the process of the present invention being capable of being carried out successfully with as low as 1% monomer, preferably 10% monomer based on the weight of the water in the aqueous electrolyte system.

As indicated previously, the polymerization process is conducted in the presence of a catalyst which provides a source of free radicals. In this respect, any of the conventional free radical initiator catalysts generally employed in vinyl polymerizations can be employed in accordance with the process of the present invention, such catalysts being added either to the mixture of monomers polymerized in accordance with the present invention or to the aqueous solution of electrolyte. Thus, for example, the catalyst can comprise any of the conventional peroxide catalysts, e.g., benzoyl peroxide, di-t-butyl peroxide, as well as the preferred azo catalysts, e.g., azobisisobutyronitrile.

The crosslinking agents which are suitably employed in the preparation of the porous bead or porous granular form of polymer in accordance with the present invention are those which contain two or more functional groups capable of taking part in the polymerization reaction so as to provide a polymeric product having a crosslinked or three dimensional structure.

Accordingly, suitable crosslinking agents that have been found particularly applicable in accordance with the present invention are the alkylenebisacrylamides, e.g., N,N'-methylenebisacrylamide, the alkylene glycol dimethacrylates, e.g., ethylene glycol dimethacrylate, diethylene glycol dimethacrylate, tetraethylene glycol dimethacrylate, higher polyethylene glycol dimethacrylate, 1,3- and 1,4-butanediol di- acrylates and dimethacrylates, etc. and the divinyl aromatic compounds, e.g., divinyl benzene, divinylethylbenzene, divinylchlorobenzene, divinyltoluene, divinyl naphthalene, etc. Other suitable crosslinking agents include allyl acrylate, p-isopropenylstyrene, trivinyl meseate, diallyl maleate, divinyl ether, 1,3- or 1,4-divinyl oxybutane, trivinyl citrate, divinyl o-phenylene diacetate, vinyl allyl ether, diethylene glycol diallyl ether, trivinyl glyceryl ether, divinyl glyceryl ether, tetravinyl pentaerythrityl ether, hexahydro-1,3,5-triacryl-s-triazine, vinylpyrrolidone dimers described in U.S. Pat. No. 3,252,995, and the like. Additionally, mixtures of the above-cited suitable crosslinking agents can be advantageously employed where desired.

As indicated above, the crosslinking agent is generally employed in an amount of from about 0.1% to about 20% by weight based upon the weight of the N-vinyl lactam or N-alkyl-N-vinylamide monomer. An amount of from about 3% to about 5% of the crosslinking agent is preferred.

Similarly, as indicated above, the N-vinyl lactam or N-alkyl-N-vinylamide can be polymerized in the presence of an optional copolymerizable monomer. Preferably such copolymerizable monomer should be present in an amount of less than about 50% by weight based on the weight of the N-vinyl lactam or N-alkyl-N-vinylamide monomer, and more preferably, in an amount of less than about 20% by weight.

Examples of comonomers which can be employed are the N-vinyllactams or N-alkyl-N-vinylamides listed above, or acrylates, e.g., methyl, ethyl, propyl and higher alkyl, phenyl, naphthyl and other aryls; α-substituted acrylates such as α-methyl, ethyl, propyl and higher alkyl, phenyl, naphthyl and other aryls; vinyl ethers, e.g., methyl, ethyl, propyl and higher alkyls, acrylamide, acrylic acid, acrylonitrile, allyl acetate, allyl alcohol, crotonic acid, dimethylaminoethylvinyl sulfide, diethylhexyl maleate, didodecyl maleate, fumaramide, itaconic acid, methacrylic acid, methacrylamide, methoxy styrene, methyl vinyl ketone, methyl vinylpyrrolidone, 2-methyl-5-vinylpyridine, styrene, trichloroethylene, vinyl carbazole, vinylimidazole, vinyl laurate, vinyl methyl benzimidazole, vinyl methyl dichloro silane, vinyl methyl oxazolidinone, vinyl oxyethylurea, vinyl propionate, vinyl pyridine, vinyl siloxanes, vinyl stearate, vinyl acetate (and the derived vinyl alcohol).

It is noted that a further description of the production of the crosslinked particulate polymeric N-vinyllactam polymers and copolymers and N-alkyl-N-vinylamide polymers and copolymers in the form of porous beads or porous granules can be found in co-pending applications Ser. No. 736,302 and 875,516. Thus, for example, the polymerization process may be carried out by adding all of the monomers to the salt solution in one charge or such monomers may be added in portions or continuously during the polymerization. The polymerization is usually carried out at about 50° to 80° C and requires a relatively short time for completion, e.g., about 2 to 6 hours. Accordingly, the disclosure of co-pending application Ser. No. 736,302 as it pertains to the production of the water-insoluble but water-swellable porous bead-like crosslinked polymers employed in the process of the present invention is herein incorporated by reference.

The above-discussed porous granular or porous bead-like crosslinked N-vinyllactams or N-alkyl-N-vinylamides according to the instant invention are then complexed with the phenolic material. The phenolic material employed in connection with the instant invention may be any soluble compound, i.e., water or organic liquid soluble containing a phenolic hydroxyl group. Therefore, the compounds which may be employed in forming the complexes of the instant invention are extremely wide in scope and not amenable to a simplified listing thereof. It is to be noted, however, that the following materials are merely representative thereof and in no way limiting on the scope of the phenolic material which may be employed in connection with the complexes of the instant invention. Such phenolic materials may be exemplified by:

Phenol
resorcinol
hydroquinone
salicylic acid
nonylphenol
p-cresol
8-hydroxyquinoline
8-hydroxyquinoline hydrochloride
citric acid
4-nitrophenol
phloroglucinol
dichlorophene
gallic acid
1,5-dihydroxynaphthalene
pyrogallol
catechol
hexachlorophene
o-chlorophenol
4-chloro-o-cresol
3-aminophenol
butyl hydroxyanisole
2-nitrophenol
n-heptyl-p-hydroxy benzoate
2,6-di-tert-butyl-p-cresol
2-hydroxy-4-methoxy-benzophenone-5-sulfonic acid
2,4-dihydroxy benzophenone
2-hydroxy-4-methoxy-benzophenone
2,2'-dihydroxy 4,4'-dimethoxy-benzophenone
2,2',4,4'-tetrahydroxy benzophenone
sodium 2,2'-dihydroxy-4,4'-dimethoxy-5-sulfo-benzophenone
o-cresol
m-cresol
and the like.

The novel complexes of the instant invention may readily be formed by contacting the crosslinked porous bead or porous granule N-vinyllactam or N-alkyl-N-vinylamide polymers with the phenolic material. That is to say, the phenolic material may be dissolved in a suitable solvent or mixture of solvents therefor in varying solution concentrations over a wide range which is subject only to the desired use of the end product. The solvent employed in the process of the instant invention would, of course, be one in which the phenolic material is soluble. The amounts employed in connection therewith are not in any way critical or limited hereby.

The novel phenolic complexes of water-insoluble, but water-swellable porous bead or porous granule crosslinked N-vinyllactams or N-alkyl-N-vinylamide polymers as noted are ideally suited for use in applications wherein a limited amount of phenolic material is desired, particularly those applications which require solutions containing up to 5,000 ppm phenolic material, preferably solutions containing up to 100 ppm phenolic material for beverages and up to 5,000 ppm for water or higher for herbicidal sprays. It is to be understood that the concentration of phenolic material in the solution subjected to treatment herein is dependent on the desired field application and what is required for an effective amount. For example, it has been found that finished beer to which 10 to 12 parts per million of N-heptyl-p-hydroxy benzoate was added, was found to be microbiologically stable. It is noted, however, that an elaborate control system is needed for the addition of said n-heptyl-p-hydroxy benzoate so as to guard in commercial installations against the precipitation of said n-heptyl-p-hydroxy benzoate in the beer and further the loss of the ratio control of additive solution flow rate to beer flow rate. The former is important because at the pH values of the beer, the additive N-heptyl-p-hydroxy benzoate tends to precipitate from the additive solution. The latter ratio is important because it would result in a beer being either over or under treated depending upon the variables in said rate. Therefore, one of the particular uses to which the novel polymeric materials of the instant invention can be put would be to incorporate a n-heptyl-p-hydroxy benzoate complex, crosslinked N-vinyllactam or N-alkyl-N vinylamide polymer in porous granular or porous bead form into a canister which would be designed to be inserted into the finished beer process. With use of such a phenolic complex, one would eliminate the need to solubilize the additive material by raising the pH for example. Furthermore, since the additive material normally must be employed in solution which can be effected only at a pH at which pH the ester linkage therein is hydrolyzed, one would also have the added advantage of being able to store the usable canisters or columns over an extended period of time whereas with solutions of n-heptylp-hydroxy benzoate, such storage is not possible. Further uses of the instant invention include the storage of phenolic complexes of polymeric porous granules in canisters or cartridges which porous granules are complexed with phenolic pesticides. Such canisters or cartridges may then be employed by attaching same to hoses, sprays, or other water sources wherein a controlled dilution would be effected. Such use of pesticides would, of course, overcome the numerous difficulties presently associated with the dilution of such pesticide materials prior to the use thereof.

Furthermore, it is noted that the use of such canisters or cartridges would inherently control the amount of pesticide material applied and therefore avoid mistakes in such dilution. Furthermore, an indicator dye may, of course, be incorporated into said canisters or cartridges in the bead bed per se so as to visably demonstrate the presence or absence of pesticide material and the relative use thereof.

An example of the above use of the novel phenolic complexes of the instant invention is a polymeric porous granule containing 4,6-dinitro-o-sec-butylphenol in a cartridge attached to a garden hose. Such a phenolic complex would be effective for the control of mites, insects and as herbicides in the control of weeds. It is also noted that the porous granules would be effective against the same pests if applied as a dry granule to the soil. In such dry use, one would incorporate a dye material into said granules so as to indicate the areas covered by said granules to the user. A further advantage of the dry granules would be that the chemical release would be prolonged and diminished during dry spells when damage could be caused by an excess thereof and increased during wet spells, which periods are also the most advantageous for weed growth.

A still further use of the novel phenolic materials of the instant invention would be in the field of industrial waste treatment and sewage treatment. For example, granules containing trichlorophenol could be employed as slimicides in paper mills. Further industrial uses of the novel complexes of the instant invention are in circulating systems or storage vats as bacteriostats and algicides. For example, canisters of porous granules treated with 2,2'-thiobis(4,6-dichlorophenol) would be effective as preservatives in cutting oils and as algicides in water treatment. 2,6-di-tert-butyl-p-cresol and butyl hydroxyanisole could also be complexed according to the instant invention and be employed in granular form as antioxidants.

In the field of home sanitation, the novel phenolic porous granular complexes of the instant invention could be employed as sanitary germicides for the maintenance of toilet bowls. In such a use, phenolic materials such as phenol or guiacol could be complexed according to the process of the instant invention.

In the field of oral hygiene, a phenolic complex of 4-n-hexyl resorcinol could be prepared with the resulting porous beads being incorporated into a small cartridge. When such a cartridge is held under tap water, a disinfectant or mouth wash is instantly provided. Cartridges containing disinfectants, tonics and antibiotics can be inserted in automatic drinking systems for poultry and cattle in a manner similar to the above. Such phenolic materials also include, oxytetracycline, chlortetracycline and saligenin.

Fungicidal materials such as 8-hydroxyquinoline or dichlorophene can be complexed within the scope of the instant invention so as to provide a porous bead or porous granular-like product which would release same. Dry granules may also be prepared which slowly release air attractants, repellents or fragrances. For example, eugenol or isoamyl salicylate may be employed as attractants in poison baits for moths and flies. Creosote may be employed as a barrier to the migration of Chinch bugs. Salicylaldehyde or vanillin may be employed as fragrances in room deodorant and other similar compositions.

The particle size of the porous granules or porous beads which result according to the process of the instant invention is not considered particularly critical thereto. It is to be noted, however, that said phenolic complexes having a 16 – 60 mesh size (U.S. Standard Sieve Series) are considered particularly well suited for use in canisters and/or columns.

The instant invention will now be illustrated by means of the following more detailed examples thereof. It is to be noted, however, that the instant invention is not deemed as being limited thereby.

EXAMPLE 1

Into a 2-gallon, stainless steel stirred autoclave the following ingredients were charged:

3.3 g. azobisisobutyronitrile previously dissolved in 660 g. of vinyl pyrrolidone; 33 g. Dow divinylbenzene mixture (50–60; Assay 55%); 2150 g. distilled water; 10 g. 10% by weight pibasic sodium phosphate buffer solution; 570 g. anhydrous sodium sulfate (Baker's Reagent Grade).

The autoclave was then purged of air by applying a vacuum to 25 mm. The vacuum was then released with nitrogen and the procedure repeated two more times. The materials were then heated with stirring (210 RPM, 4 blade turbine) to 65° C over a period of one hour and held at said temperature for a period of three hours at a pressure of 3 to 4 Psig. A side flange was removed from the autoclave, and a dispersion of 1.5 g. azobisisobutyronitrile in 50 mls. of C.P. ethanol were added through the port. The flange was then replaced and the reaction continued for an additional hour at 65° C. The temperature was then raised to 85° C over a period of ½ hour and then held at that temperature for an additional 2 hour period (8 to 10 Psig). The reaction product was then cooled and discharged into a Buchner funnel and washed with distilled water to remove any remaining sodium sulfate until a portion of the filtrate was tested with a few millimeters of saturated barium chloride solution and was found to be less turbid than a barium chloride control test with tap water. After allowing the excess water to drain, the wet porous beads weighed 3125 grams. A 100 gram portion of these porous beads were then dried in a high-vacuum oven at a temperature of between 65° and 70° C, and the dried porous beads again weighed, so as to determine a 95.1% yield.

EXAMPLE 2

Into a 500 ml. resin flask equipped with thermometer, stirrer, gas inlet, dropping funnel, and condenser connected to gas outlet were charged:

40.0 g. (0.36 mole) distilled vinylpyrrolidone
0.12 g. azobisisobutyronitrile
240.0 g. distilled water 1.6 g. (0.010 mole) methylenebisacrylamide
0.46 g. 10% by weight $Na_2HPO_4$ solution
40.0 g. anhydrous sodium sulfate Air was removed by closing the gas inlet and applying enough vacuum at the gas outlet to cause violent ebullition for 30 seconds. The vacuum was then released by allowing nitrogen to enter the gas inlet. This procedure was repeated two more times and then a positive pressure of nitrogen maintained by connecting the gas outlet to a mineral oil blow-out leg having a depth of one inch of oil. The flask was heated with stirring in a constant temperature bath for 4 hours at a reaction temperature of 50° to 65° C. At the end of this time a solution of 0.04 g. azobisisobutyronitrile
0.4 g. methylenebisacrylamide
10.0 g. C.P. ethanol
10.0 g. distilled water was charged to the dropping funnel and the air removed by violent ebullition and replaced with nitrogen. This procedure was repeated two more times by suitable adapters connected to the dropping funnel.

The above solution was then added to the contents of the flask and the heating continued for 2 additional hours at 62° to 65° C. At the end of this time the beads produced were filtered and washed with 1 gallon of distilled water and then dried in a vacuum oven at 40° C.

The dried white porous beads weighing 41.5 grams (98.8% yield), were substantially ash-free, whiteness being due to the light scattering caused by the pores within the beads. The porosity was confirmed by microscope examination.

EXAMPLE 3

Following the procedure of Example 2,
40.0 g. (0.36 mole) distilled vinylpyrrolidone
0.4 g. azobisisobutyronitrile
200.0 g. distilled water
1.2 g. ethylene glycol dimethacrylate
0.5 g. 10% by weight $Na_2HPO_4$ solution
33.0 g. anhydrous sodium sulfate
were charged to the resin flask and heated with stirring at a reaction temperature of 50° to 69° C for a total of 5¼ hours.

The porous beads were filtered and washed with 1 gallon distilled water and dried in a vacuum oven at 45° to 50° C.

The dried white porous beads weighed 39.0 grams (94.6% yield).

EXAMPLE 4

Following the procedure of Example 2,
40.0 g. (0.36 mole) distilled vinylpyrrolidone
0.12 g. azobisisobutyronitrile
240.0 g. distilled water
2.0 g. tetraethylene glycol dimethacrylate
1.0 g. 10% by weight $Na_2HPO_4$ solution
40.0 g. anhydrous sodium sulfate
were charged to the resin flask and heated with stirring at a reaction temperature of 50° to 67° C for a total of 5 hours. The washed and dried porous beads weighed 39.2 g. (93.3% yield).

EXAMPLE 5

Following the procedure of Example 2,
40.0 g. distilled vinylpyrrolidone
0.12 g. azobisisobutyronitrile
240.0 g. distilled water
6.0 g. polyethylene glycol dimethacrylate
2.0 g. 10% by weight solution of $Na_2HPO_4$
40.0 g. anhydrous sodium sulfate
were charged to the resin flask and heated with stirring at a reaction temperature of 50° to 68° C for a period of 5¾ hours. The washed and dried beads weighed 40.0 grams (86.9% yield).

EXAMPLE 6

Following the procedure of Example 2,
40.0 g. distilled vinylpyrrolidine
0.16 g. azobisisobutyronitrile
132.0 g. distilled water
1.6 g. p-divinylbenzene (99% purity of Shell Oil Co.)
0.14 g. 10% by weight $Na_2HPO_4$
35.0 g. anhydrous sodium sulfate
were charged to the resin flask and heated with stirring at a reaction temperature of 50° to 84° C for a period of 4.0 hours.

50 ml. methanol were added and stirred for ½ hour at 75° C then filtered and washed as before. The dried porous beads weighed 41.6 g. (100% yield).

EXAMPLE 7

Production of Copolymer of 60 parts vinylpyrrolidone
40 parts acrylamide crosslinked with divinylbenzene
The following reactants were charged into a 1 liter stainless steel autoclave equipped with a 4 blade turbine type stirrer:

96.0 g. vinylpyrrolidone
8.0 g. divinylbenzene Dow DVB-55 (a mixture of isomers of divinylbenzene, ethyl vinylbenzene, and diethylbenzene, the total divinylbenzene content being 55.0%.)
520.0 g. distilled water
2.8 g. 10% by weight $Na_2HPO_4$ solution
0.64 g. azobisisobutyronitrile
140.0 g. anhydrous sodium sulfate
64.0 g. acrylamide The autoclave was evacuated to 25 mm and the vacuum released with nitrogen. This procedure was repeated two more times. The contents of the autoclave were then heated with stirring to 90° C and held at that temperature for 3 hours. The porous beads were discharged, washed free of sodium sulfate and dried. The product yield was 151 g. (or 90% yield).

EXAMPLE 8

99 parts vinylpyrrolidone 1 part acrylimide crosslinked with divinylbenzene
The following reactants were charged with a 1 liter stainless steel autoclave and treated in a manner similar to Example 9.

118.8 g. vinylpyrrolidone
1.2 g. acrylamide
390.0 g. distilled water
0.5 g. azobisisobutyronitrile
6.0 g. DOW DVB-55 divinylbenzene
105.0 g. anhydrous sodium sulfate
0.4 g. 10% by weight $Na_2HPO_4$ solution The copolymer was produced in a yield of 94.7%.

EXAMPLE 9

A phenolic complex containing 8-hydroxyquinoline was prepared by adding 2.96 grams of the dry porous beads of Example 1 to a solution of 2.50 grams of 8-hydroxyquinoline dissolved in 50 mls. of C.P. ethanol. The resultant slurry was mixed for approximately 19 hours, filtered, and dried under vacuum for three days. The dried polymer complex weighed 3.4 grams and was found by acid titration to contain 14.5 grams of 8-hydroxyquinoline.

EXAMPLE 10

A phenolic polymeric complex was prepared according to the process of Example 9 except that 5.0 grams of 8-hydroxyquinoline were dissolved in ethanol in lieu of 2.5 grams thereof. The dried polymer weighed 3.8 grams and the granules were found by titration to contain 23.9% 8-hydroxyquinoline. The gradual release of the phenolic material from the complex was demonstrated as follows:

25 grams of dry porous granules prepared according to Example 9 except that said granules contained 27.5% of 8-hydroxyquinoline, were wetted in 500 mls. distilled water and charged into a glass column. Distilled water was then passed through the resin bed at a steady rate of 10 mls. per minute. The effluent liquid was collected in 500 ml. portions and titrated for available 8-hydroxyquinoline. Each fraction contained approximately 700 PPM of 8-hydroxyquinoline for the first 18 fractions (a total of 9 liters of that effluent) after which a reduction in concentration was noted due to the exhausting content of the polymer bed.

EXAMPLE 11

2.96 grams of polymer porous granules prepared according to Example 1 were slurried in a 10% solution of n-heptyl-p-hydroxybenzoate in C.P. ethanol for 19 hours, filtered and dried for 7 days in a high vacuum at 45° C. It was found that 1.44 grams of n-heptyl-p-hydroxybenzoate had been absorbed by the porous granules.

EXAMPLE 12

The following phenolic materials were complexed as in Example 10 and found to form a complex with the porous granular beads of Example 1. The phenolic materials complexed included:
phenol
nonyl phenol
salicylic acid
1,5-dihydroxy naphthalene
butylhydroxy anisole
2-nitrophenol
2,6-di-tert-butyl-p-cresol
4,6-dinitro-o-sec-butyl phenol
trichlorophenol
2,2'-thiobis(4,6-dichlorophenol)
4-n-hexylresorcinol
chlorotetracycline
vanillin.

EXAMPLE 13

Example 1 was repeated except for the use of N-methyl-N-vinylacetamide instead of N-vinylpyrrolidone. The product was treated as in Example 12 to produce a variety of phenolic complexes

Having thus described the method of making the porous granules or beads which are phenolic complexes of water-insoluble but water-swellable crosslinked N-vinyllactam or N-alkyl-N-vinyl amide polymers, reference is now had to containers which are utilized to provide gradual release of phenolic material in a fluid environment from said porous granules or beads in a sustained phenolic release system.

It is to be understood that the following description in connection with the accompanying drawings illustrates a few specific embodiments of this invention but that many other variations and modifications will be apparent from this description and disclosure which are also included in the scope of the invention.

Figure 1:
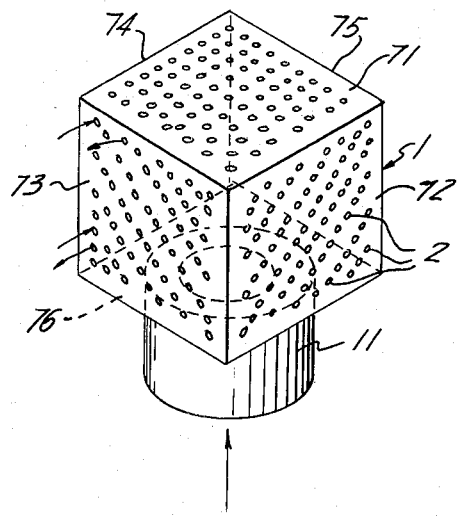
FIG. 1 is a perspective view of one embodiment of the container.

Referring now to FIG. 1 the container is substantially cubical having a top surface 77, a bottom 76 and side walls 72, 73, 74 and 75 all joined to form the cube shown. Each of the side walls, the top and bottom are perforated with apertures 2. The apertures 2 are uniformly spaced over the surface of the walls and each has a diameter smaller than the diameter of the porous granules contained within the container in a contact zone. Inlet conduit 11 is connected to the bottom 76 of the canister 1 and terminates therewithin for delivery of fluid into the central lower portion of said contact zone. The apertures 2 allow emission of fluid after contacting the granules in the packed canister and leaching some of the phenolic material from the phenolic complexed beads or granules within the container. It is to be understood that in this embodiment, side walls 72, 73, 74 and 75, as well as the top 71 and bottom 76 of the container, may be perforated to permit emission of fluid. Alternatively, nonperforated sides formed of solid plates can be provided instead of all but one of the walls. It will become apparent that the canister of FIG. 1 may be designed to omit inlet conduit 11, in which case liquid would enter and exit from the apertures 2 of the canister after contacting the granules. This adaptation would be ideally suited for a bactericidal cartridge for use in a water closet tank.

Figure 2:
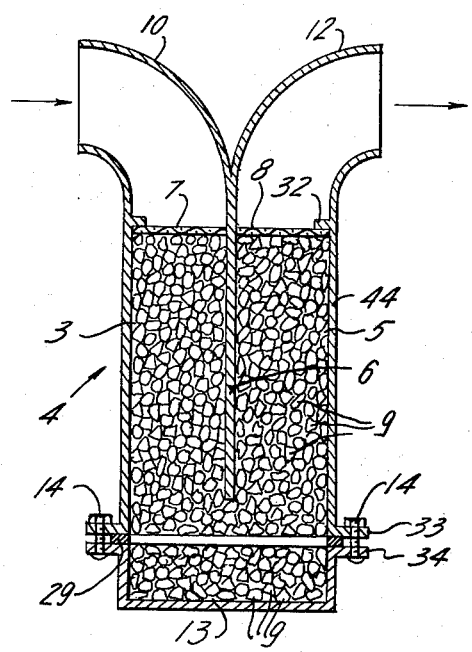
FIG. 2 is a cross-sectioned view showing another embodiment of the container.

FIG. 2 shows another container 4 formed of a cylinderical housing 44 with inlet conduit 10, outlet conduit 12 and having weir 6 terminating above the base of the flanged open bottom end of the container and dividing the container into two upper compartments or chambers 3 and 5 which are in open communication at their base. A flanged open ended lower chamber 13, forms the bottom section of the container. The top portion of each chamber 3 and 5 is covered by perforated metal, or abrasion resistant, screens, grids or webbing designated as 7 and 8 each having a plurality of apertures of smaller diameter than the diameter of the porous granules 9 which are contained in the chambers below the grids. Members 7 and 8 are positioned by seat 32 at the top section of the cylindrical housing 44 of canister 4.

Fluid inlet means 10 is positioned above grid 7 covering first chamber 3 containing porous granules 9, and fluid outlet means 12 is positioned above grid 8 covering chamber 5 to permit withdrawal of said fluid from said chamber after passing downwardly through chamber 3 and traversing chamber 13 in contact with the porous granules 9. Lower chamber 13, which has a closed base and is in open communication with chambers 3 and 5, is flanged at its upper open end and is secured to the upper portion of the container through the flanges 33 and 34 interposed with sealing gasket 29 by bolting means 14. In this embodiment, fluid enters inlet 10 and passes successively through chambers 3, 13 and 5 wherein it is contacted with the porous granules which release phenolic material into the fluid environment before exiting from said container at outlet 12.

As a modification of this embodiment, weir 6 can be a common wall between conduit means 10 and 12 or it can be disposed as a separate plate interposed therebetween and adapted to be raised or lowered to shorten or lengthen chambers 3 and 5 thereby increasing or restricting the flow of fluid therethrough and consequently decreasing or increasing the residence time of the fluid within the contact zone.

Figure 3:
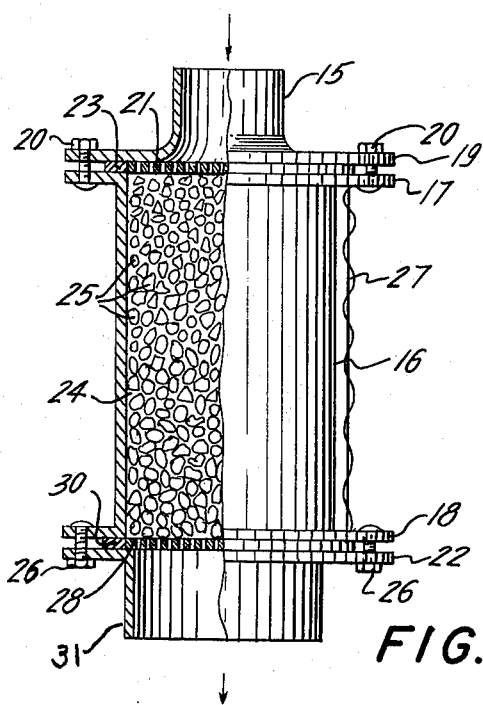
FIG. 3 is a partial side elevational view, partial sectional view showing a further embodiment of the present invention.

FIG. 3 illustrates still another embodiment of the present invention which is readily disassembled for replacement of components of the apparatus and/or porous granules contained therein. Conduit 15 is equipped with an outwardly extending flange 19 and represents fluid inlet means. Fluid permeable chamber 16 is flanged at its upper end with outwardly extending flange 17 adapted for connection with flange 19 through belting means 20. Perforated grid 21, having a plurality of openings of smaller diameter than the diameter of the porous granules 25 and having an annular sealing gasket 23 around its circumference is positioned in the top portion of the fluid permeable chamber 16 and interposed between flanges 17 and 19. Chamber 16 is also flanged at its lower end with outwardly extending flange 18. Conduit 20, representing fluid withdrawal means, is equipped with an outwardly extending flange 22 which is adapted to be secured to flange 18 through bolting means 26. Grid 28, having a plurality of openings of smaller diameter than the diameter of the porous granules in the lower portion of chamber 16 and having annular sealing gasket 30 around its circumference, defines the base portion of chamber 16 and is interposed between flanges 22 and 18. In this particular embodiment, there is shown a heating element 27 which may be adapted to be wound around the shell of contact chamber 16 for increasing dissolution of the phenolic material in the fluid by temperature control. It is to be understood, however, that the use of such heating element is optional.

In this embodiment the fluid, preferably water or a liquid beverage, enters the container from inlet conduit 15, passes through grid 21 and enters contact chamber 24 containing porous granules 25 of phenolic complexed water-insoluble, water-swellable crosslinked N-vinyllactam of N-alkyl-N-vinylamide polymer before exiting through outlet 31. During passage of the fluid through chamber 24 in contact with granules 25 a portion of the phenolic material of the complex is leached into the fluid environment, the amount being controlled by the rate of fluid flow through the chamber and the surface area of the granules.

Generally the rate of fluid flow is maintained between about 2 and about 50 mls per minute and the particle size of the granules in the contact zone is between about 0.5 and about 40 mesh size (U.S. Standard Sieve Series). It is to be understood that the liquid flow in the container illustrated can be reversed so that the liquid enters conduit 20, percolates upwardly through the granules in chamber 16 and is withdrawn through conduit 15.

Figure 4:
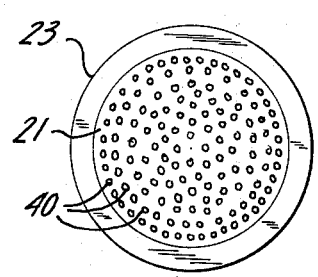
FIG. 4 is a plan view of the grid element shown in FIG. 3.

FIG. 4 shows in plain view the grid 21 used in the container shown in the embodiment of FIG. 3, having apertures 40 of a smaller diameter than the diameter of the granules retained in the contact chamber by said grid. Grid 21 is surrounded by sealing gasket 23 of a suitable sealing material.

It is to be understood that the assembly illustrated in FIG. 3 may contain one or more grids internally spaced within contact chamber 24 to support said porous granules and to retard the flow of fluid for longer residence time therein. Also a plurality of contact chambers may be used in series by having conduit 31 represent a fluid transfer line for passing fluid from one container to the next identical container, which containers are joined in series through flanges similar to 19 and 17 having interposed sealing gaskets.

Figure 5:
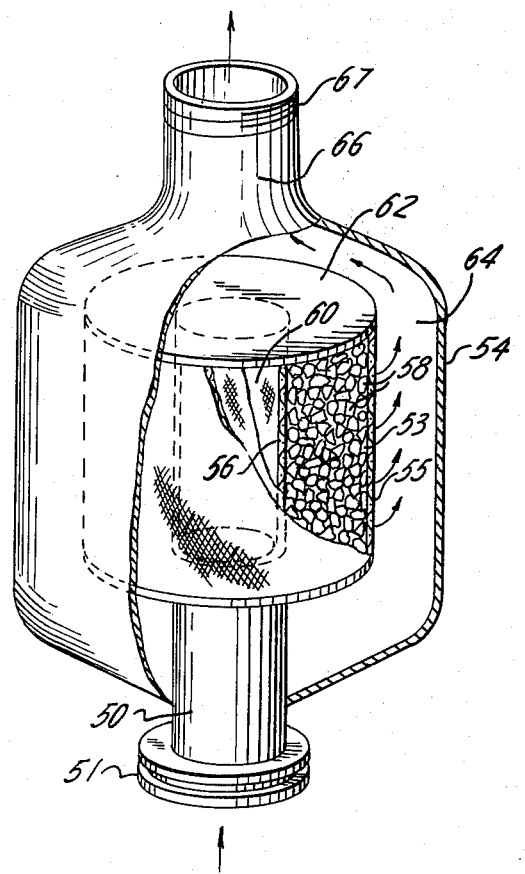
FIG. 5 is a perspective view with portions in section, showing yet another embodiment of the present invention.

FIG. 5 illustrates a disposable type plastic canister adapted for connection between a garden hose and a nozzle when the canister is used as a herbicidal spraying device. In this embodiment fluid inlet means 50 is equipped with a coupling 51 suitable for substantially seal-proof attachment to a garden hose. Enlarged plastic housing 54 is continuous with, or attached to, inlet means 50 and encloses, in spaced relationship thereto, a contact zone 53 defined by outer and inner surfaces of cylindrical screens 55 and 56, respectively. Porous granules 58, of larger mesh size than the openings of the screens, are disposed in contact zone 53 between the inner and outer respective surfaces of the screen cylinders.

Inlet means 50 is designed to terminate and be integrally joined to the upstream end of inner screen 56 so as to introduce fluid into central cavity 60 formed by the inner circumference of screen 56.

The downstream end of cylindrical screens 55 and 56 is capped with solid annular plate 62 so that fluid in cavity 60 is formed to exit through screen 56, contact granules 58 in chamber 53 and leave the contact zone through screen 55 from which the fluid travels upwardly in annular channel 64 formed by the space between the outer surface of screen 55 and the inner wall of housing 54. The fluid then enters a restricted outlet portion 66 of the housing 54 which outlet portion is threaded 67 at its upper open end for attachment to a garden spray nozzle or similar spraying device.

In the above description, it will become apparent that the containers illustrated by the above Figures may be cylindrical, cubical or of any other desirable shape and size and the fluid can be passed through the contacting zone in a direction reverse to that shown. Many other variations and modifications of the present invention will become obvious to those skilled in the art from the present disclosure.

What is claimed is:

1. A sustained phenolic releasing system which comprises a container containing porous granules or beads comprising a complexed compound of a phenolic material with a water-insoluble, but water swellable crosslinked polymer of a N-vinyllactam or an N-alkyl-N-vinylamide and provided with means permitting continuous flow of a fluid in which said phenolic material is soluble or readily dispersable into said container, contact with said granules or beads contained therein for a time sufficient for said fluid to leach a desired amount of the phenolic material from the porous granules and exit from said container.

2. The system of claim 1 wherein the container comprises an internal, liquid permeable chamber containing said porous granules and wherein said means permitting said fluid to continuously enter and leave said container consists of separate inlet means and outlet means, said inlet means being situated at one end of said container upstream of said liquid permeable chamber and said outlet means being situated at the opposite end of said container downstream of said liquid permeable chamber whereby a liquid in which said phenolic material is soluble or readily dispersible is introduced into said inlet means of said container and is successively passed through the liquid permeable chamber in contact with said porous granules and through said liquid outlet means in a manner such that phenolic material is continuously absorbed by the fluid from the porous granules and a phenolic container liquid is withdrawn from said container.

3. The system of claim 2, wherein said inlet means is adapted to pass the liquid upwardly to permit percolation of the porous granules in its upward passage through the contact chamber.

4. The system of claim 3, wherein the inlet means is regulated to pass water through the chamber at a rate sufficient to permit withdrawal of liquid containing up to 5,000 ppm phenolic material.

5. The system of claim 3, wherein the inlet means is regulated to pass a beverage through the container at a rate sufficient to permit withdrawal of beverage containing up to 100 ppm phenolic material.

6. The system of claim 2 wherein the liquid permeable chamber is bounded by a pair of perforated grids having openings of a smaller dimension than the porous granules contained therein, said grids being positioned downstream of said inlet means and upstream of said outlet means and in spaced relationship to each other.

7. The system of claim 2 wherein the inlet means, the outlet means and the liquid permeable chamber are adapted to be joined together through outwardly radiating flanges secured by fastening means, the liquid permeable chamber is bounded by a pair of grids, the first of which is positioned between the upstream flange of the liquid permeable chamber and flange of the inlet means and the second of which is positioned between the downstream flange of the liquid permeable chamber and the flange of the outlet means, said grids having openings of smaller dimensions than of the porous granules contained in the chamber, whereby said grids and said liquid permeable chamber can be readily disassembled by releasing said fastening means joining the flanges of the liquid permeable chamber to said inlet and outlet means.

8. The system of claim 1 wherein the porous beads or granules have a particle size between about 0.5 and about 40 mesh size (U.S. Standard Siev Series).

9. The system of claim 1, wherein the means for introducing fluid is regulated so as to pass fluid through the container at a flow rate of between about 2 and 50 mls. per minute 10. A container containing porous granules or beads comprising a complex compound of a phenolic material with a water-insoluble, but water-swellable crosslinked polymer of an N-vinyl lactam or an N-alkyl-N-vinyl amide and provided with means permitting a fluid, in which said phenolic material is soluble or readily dispersible, to enter said container, contact said granules or beads contained therein and leave said container.

* * * * *